US00PP26731P3

(12) United States Plant Patent
Avizohar

(10) Patent No.: US PP26,731 P3
(45) Date of Patent: May 17, 2016

(54) ***PAPAYA* TREE NAMED 'AURORA'**

(50) Latin Name: ***Carica papaya* L.**
Varietal Denomination: AURORA

(71) Applicant: Assaf Avizohar, Ein HaCarmel (IL)

(72) Inventor: Assaf Avizohar, Ein HaCarmel (IL)

( * ) Notice: Subject to any disclaimer, the term of this patent is extended or adjusted under 35 U.S.C. 154(b) by 115 days.

(21) Appl. No.: 14/120,688

(22) Filed: Jun. 17, 2014

(65) Prior Publication Data

US 2015/0366115 P1 Dec. 17, 2015

(51) Int. Cl.
*A01H 5/00* (2006.01)

(52) U.S. Cl.
USPC ..... Plt./156

(58) Field of Classification Search
USPC ..... Plt./156
See application file for complete search history.

(56) References Cited

PUBLICATIONS

PLUTO Plant Variety Database Dec. 2, 2015.*
Printout of prior application information for Israel Plant Breeder's Rights Grant No. 3288, issued Jun. 23, 2013 (retrieved from upov.int/pluto/en) (1 pg.).
Printout of prior application information for Community Plant Variety Office application No. 2013/3018 filed Nov. 27, 2013 (retrieved from cpvoextranet.cpvo.europa.eu) (1 pg.).

* cited by examiner

*Primary Examiner* — Annette Para
(74) *Attorney, Agent, or Firm* — Foley & Lardner LLP

(57) ABSTRACT

A new and distinct variety of *Carica papaya* plant named 'AURORA', particularly characterized by its vigorous growth; year-round high yield; parthenocarpic, globose to slightly elongated fruit of 600 g on average; medium orange, juicy, firm flesh with rich taste and no aftertaste; and suited to mediterranean growing conditions.

5 Drawing Sheets

Figure 1:
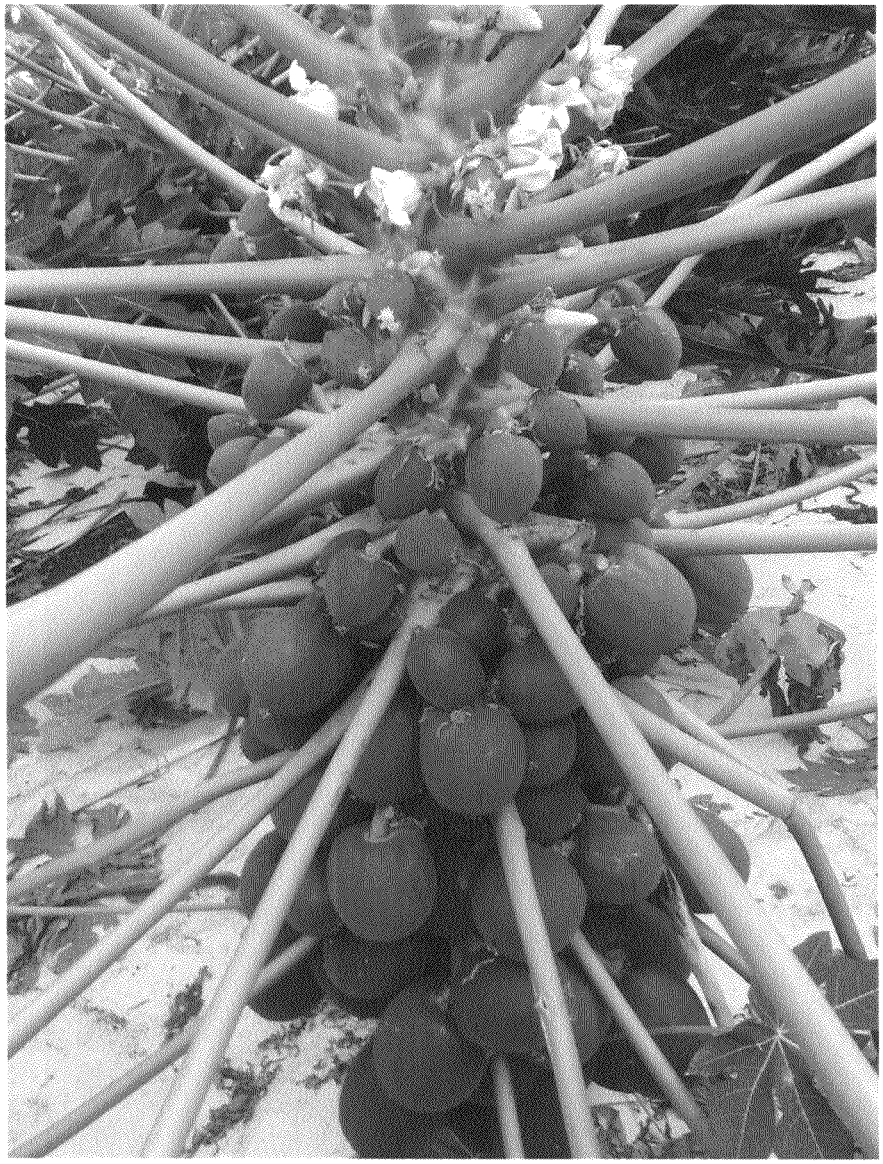

Botanical name of the genus and species of the plant claimed: *Carica papaya* L.
Variety denomination: 'AURORA'.

BACKGROUND OF THE INVENTION

The present invention relates to a new and distinct variety of a *papaya* plant, botanically known as *Carica papaya* L., the only species of the single genus of the Caricacea family, and hereinafter referred to by the denomination 'AURORA'.

The new *Carica papaya* variety is a product of a planned breeding program conducted by the inventor, Assaf Avizohar, in Hakfar Hayarok, Ramat Hasharon Israel. The objective of the breeding program was to develop a new *Carica papaya* variety suitable for subtropical climate, with parthenocarpy, regular fruit with an average weight of 600 g, having a mild taste without aftertaste, and high yield.

The new *Carica papaya* variety originated from a cross made by the inventor in the year 2005 in Ramat Hasharon, Israel. The female or seed parent is the *Carica papaya* variety 'MALKA', unpatented. The male or pollen parent is the *Carica papaya* designated 'SUNRISE', unpatented. The new *Carica papaya* 'AURORA' was observed and selected by the inventor within the progeny of the stated cross in a controlled environment in the year 2005 in Ramat Hasharon, Israel.

The new *Carica papaya* 'AURORA' was selected by the inventor based on suitable fruit size and fruit shape, high yielding and year-round parthenocarpic i.e. seedless fruit, having a good orange color and mild taste.

Asexual propagation of the new *Carica papaya* variety by meristem culture was first performed in 2009 in Kibbutz Bet Haemek, Israel, and has demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'AURORA', which in combination, distinguish this *papaya* plant as a new, unique and distinct variety: having.

1. vigorous growth;
2. year-round high yield;
3. parthenocarpic, globose to slightly elongated fruit of 600 g on average;
4. medium orange, juicy, firm flesh with rich taste; without aftertaste and
5. suitable for mediterranean growing conditions.

In comparison to the female or seed parent, 'MALKA', and the male or pollen parent 'SUNRISE', 'AURORA' differs primarily in the traits listed in Table 1.

TABLE 1

Comparison with parent varieties.

| Trait | New Variety 'AURORA' | Female Parent 'MALKA' (unpatented) | Male Parent 'SUNRISE" (unpatented) |
|---|---|---|---|
| Sex expression | parthenocarpic | female | hermaphrodite |
| Color | dark orange | pale yellow | dark orange |
| Fruit shape | round to slightly elongated | elongated | pear-shaped |
| Taste | rich | flat | mild |

Of the many commercial varieties known to the present inventor, the most similar in comparison to the new *Carica papaya* 'AURORA' is the variety 'PARADISE' (unpatented) which mainly differs from the new *papaya* 'AURORA' as shown in the table below.

TABLE 2

| Comparison with most similar variety. | | |
|---|---|---|
| Characteristic | New Variety 'AURORA' | Comparison Variety 'PARADISE' (unpatented) |
| Sex expression | parthenocarpic | female |

BRIEF DESCRIPTION OF THE PHOTOGRAPHS

The accompanying photographs illustrate the overall appearance of the new *Carica papaya* variety 'AURORA' showing the colors as true as is reasonably possible with colored reproductions of this type. Colors in the photographs may differ slightly from the color values cited in the detailed morphological description, which accurately describe the color of 'AURORA'.

FIG. 1—shows an about 1 year-old fruit bearing plant of 'Aurora'

Figure 2:
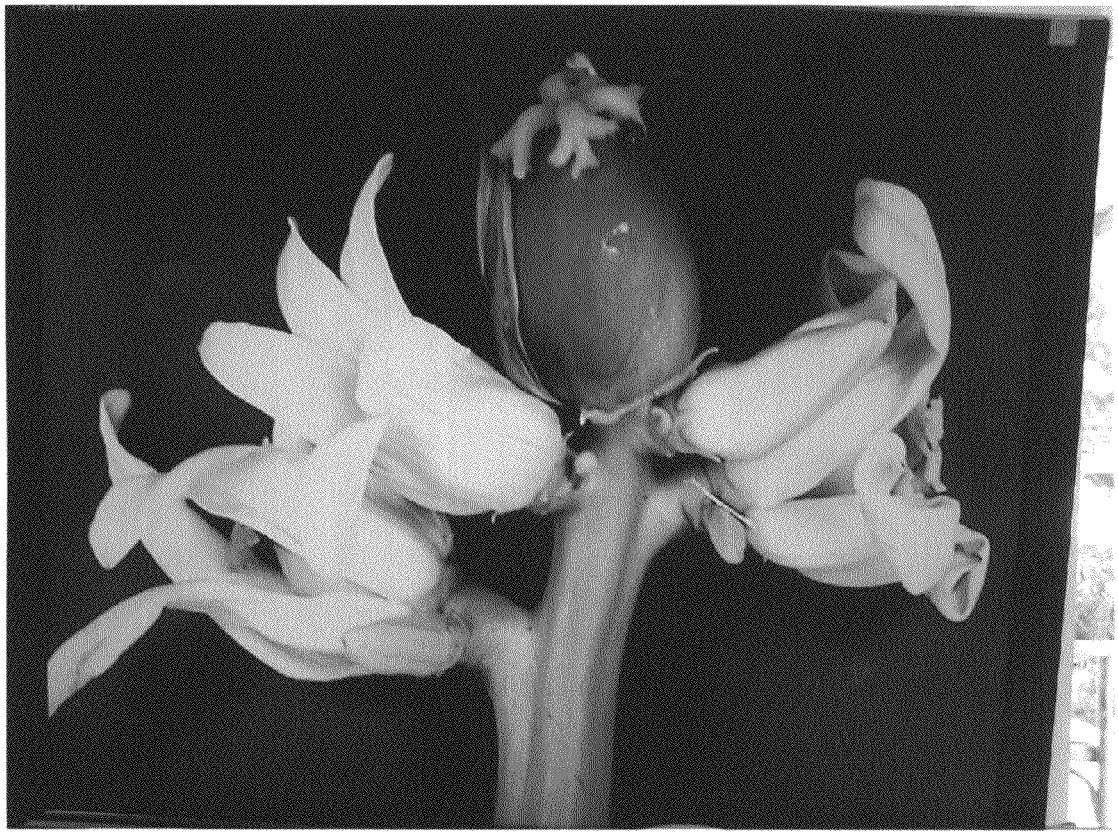

FIG. 2—shows a close-up of a typical inflorescence of 'Aurora'

Figure 3:
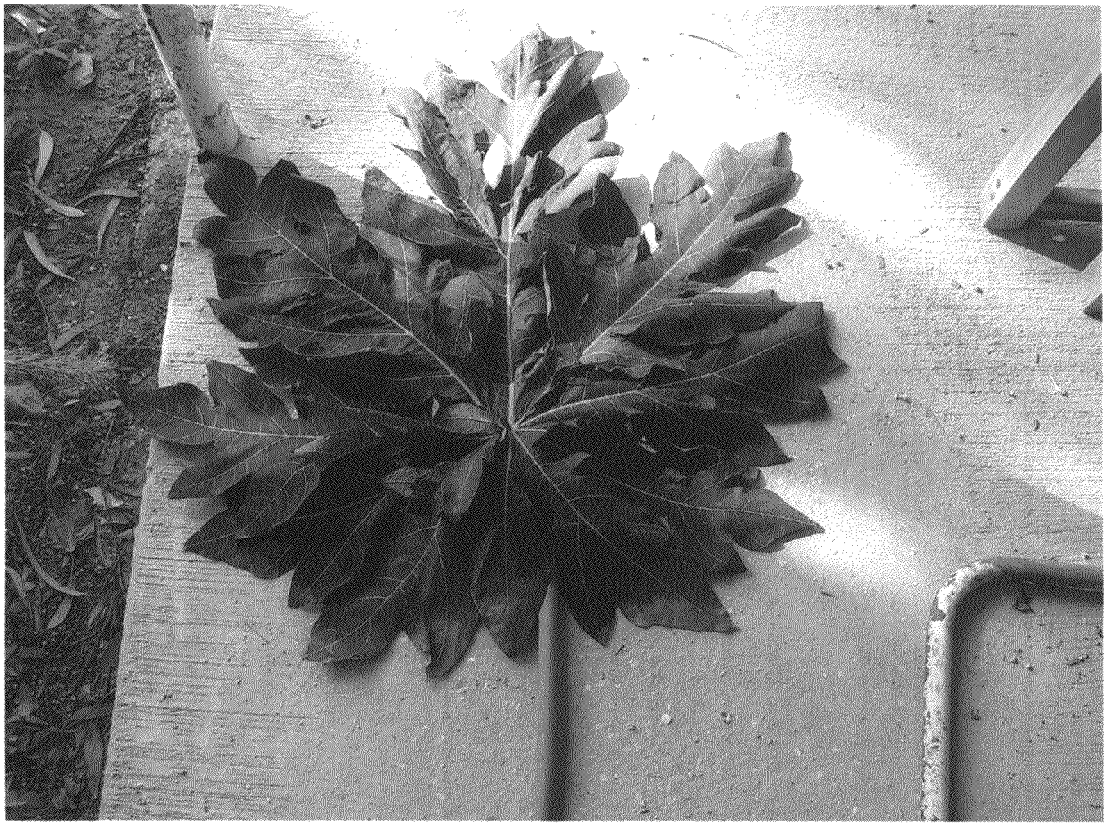

FIG. 3—shows a typical leaf of 'Aurora'

Figure 4:
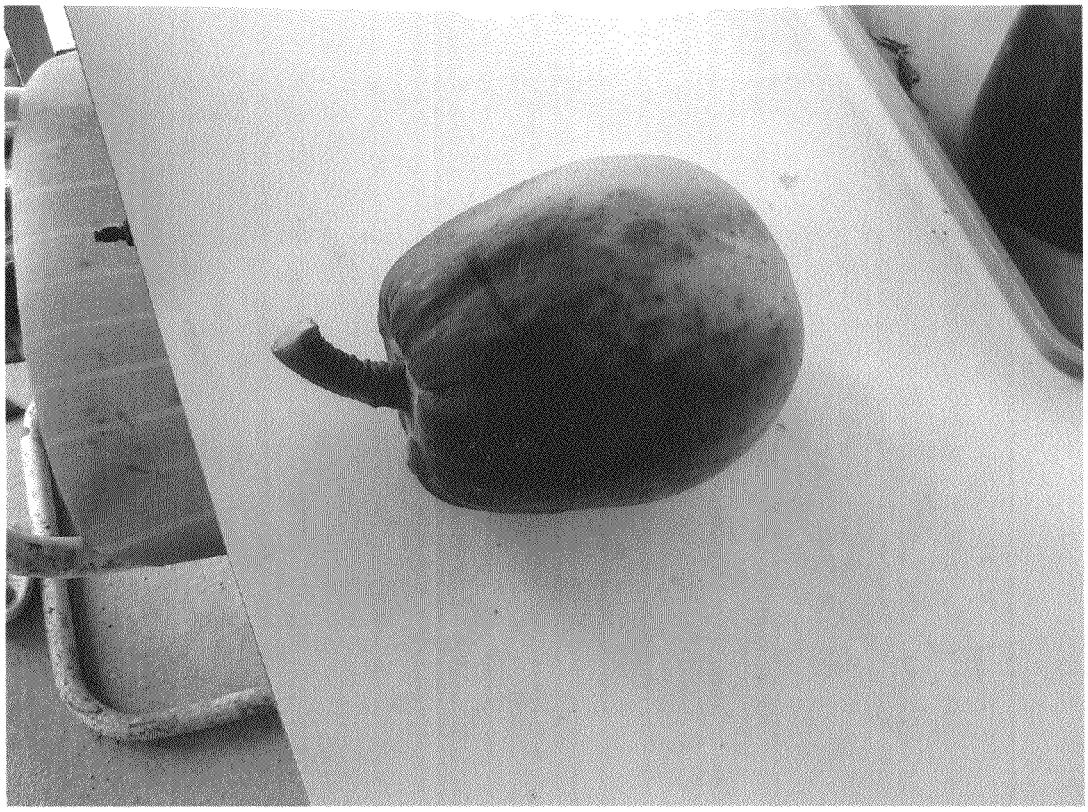

FIG. 4—shows a typical fruit of 'Aurora'

Figure 5:
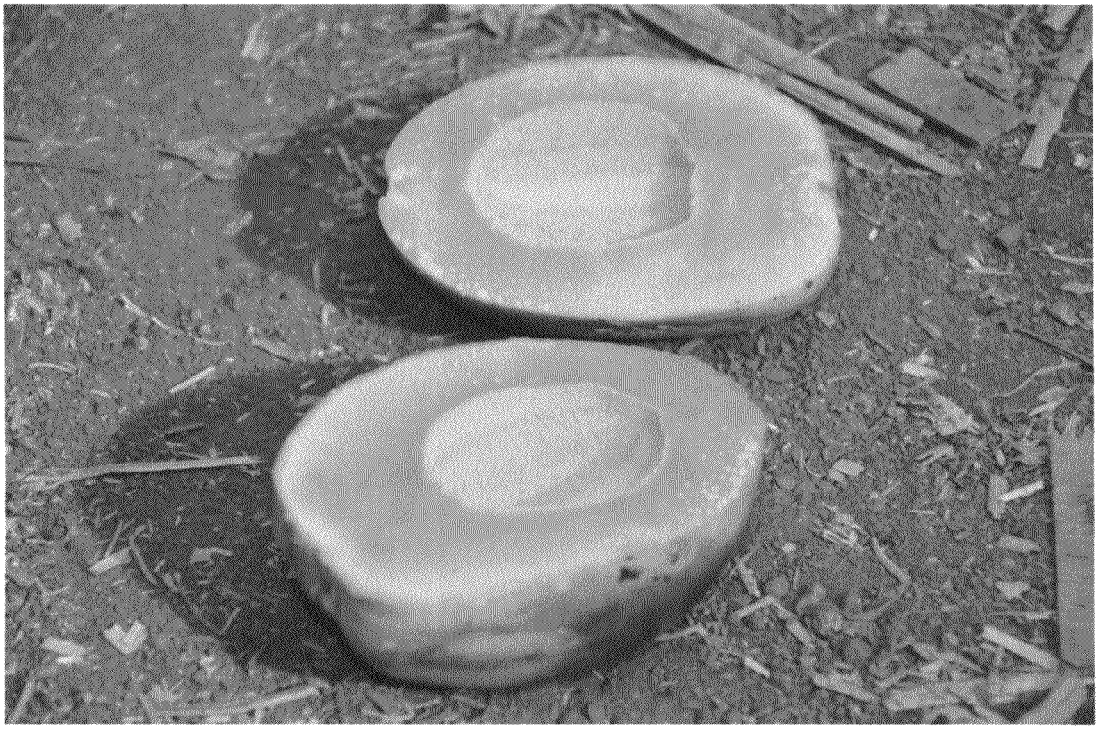

FIG. 5—shows a longitudinal section of a ripe fruit of 'Aurora'

DETAILED BOTANICAL DESCRIPTION

The new *Carica papaya* 'AURORA' has not been observed under all possible environmental conditions. The phenotype of the new variety may vary with variations in environment such as temperature, light intensity, day length, soil or pruning without any change in the genotype of the *papaya* plant.

The aforementioned photographs, together with the following observations, measurements and values describe plants of 'AURORA' as grown in the Hof Carmel, Israel, under conditions which closely approximate those generally used in commercial practice. Unless otherwise stated, the detailed morphological description includes observations, measurements and values based on 1.5-year-old plants of 'AURORA' grown in Hof Carmel, Israel. Quantified measurements are expressed as an average or a range of measurements taken from a number of plants of 'AURORA'. The measurements of any individual plant, or any group of plants, of the new variety may vary from the stated average or range.

Color references are made to The Royal Horticultural Society Colour Chart (R.H.S.), 1986 edition, except where general colors of ordinary significance are used. Color values were taken under daylight conditions in full sunlight in Hof Cannel, Cannel region, Israel.

All of the plants of 'AURORA', insofar as they have been observed, have been consistent in all the characteristics described below.

TABLE OF CHARACTERISTICS

Classification:

*Botanical.*—*Carica papaya.*

Parentage:

*Female or seed parent.*—*Carica papaya* 'MALKA' (unpatented).

*Male or pollen parent.*—*Carica papaya* 'SUNRISE' (unpatented).

Propagation: Meristem culture/rooted cuttings.

Growing conditions:

*Light intensities.*—Full sunlight.

*Temperatures.*—Between April and October average day temperature is 25° C. to 33° C. During November to March average day temperature 5° C. to 17° C.

*Planting distance.*—2.5×2.10 m.

*Soil.*—Loam.

*Irrigation.*—In greenhouse during winter 20 m3/ha, during summer 40 m3/ha.

*Fertilization.*—A balanced fertilizer with level of NPK 7-3-7, with addition of micro-elements.

*Growth regulators.*—None used.

*Pruning.*—No pruning or support needed. When the trees are freely grown, the size and the shape assumed by the trees are typical of *Carica papaya.*

Plant height: 2.7 m.

Branching: 2 or 3 incidental sideshoots on lower part of stem.

Stem:

*Structure.*—Hollow.

*Color.*—Young Plant: Green, RHS 143B. Mature Plant: Greyed-Green RHS 198 B.

*Diameter* (*at* 50 *cm height*).—About 20 cm.

*Thickness of lignified wall.*—About 5 cm.

*Amount of nodes.*—Numerous.

*Position of nodes.*—In spiral.

*Distance between two nodes in the same radial position.*—In winter 5 cm; in summer 18 cm.

*Surface texture.*—Cracked.

*Color of cracks in surface.*—Grey-brown RHS 199 A.

Leaves:

*Shape.*—Lobed, circular.

*Overall length.*—60-75 cm.

*Overall width.*—60-75 cm.

*Ratio length/width.*—1.

*Number of lobes per leaf.*—7, 8 or 9.

*Tertiary lobes.*—Absent.

*Lobe overlapping.*—Very strong.

*Leaflets.*—Absent.

*Maximum length of central lobe.*—50-55 cm.

*Maximum width of central lobe.*—20-30 cm.

*Central lobe shape.*—Spindle shaped.

*Central lobe apex.*—Acute.

*Maximum length of side lobe.*—30-38 cm.

*Maximum width of side lobe.*—18-23 cm.

*Color.*—Upper side: Green, RHS 137 A. Lower side: Green, RHS 137 C.

*Venation.*—Present.

*Prominence of veins on upper side.*—Level with surface of leaf.

*Prominence of veins on lower side.*—Very prominent.

*Color.*—Upper side: Yellow-green, RHS 145 C. Lower side: Yellow-green RHS 145 B.

*Pubescence.*—None.

*Blistering.*—Absent.

*Glossiness.*—Absent.

Petiole:

*Length.*—80-100 cm.

*Diameter* (*at base*).—About 20 mm.

*Diameter* (*adjunction to leaf blade*).—About 16 mm.

*Shape in cross section*.—Circular.
*Structure*.—Hollow.
*Thickness of wall*.—2-3 mm.
*Color*.—Yellow-green, RHS 144 B.
*Anthocyanin coloration*.—Weak.
*Pubescence*.—None.
*Waxiness*.—None.

Inflorescence:
*Time to flower*.—About one year after planting.
*Flowering season*.—Year-round.
*Height of attachment of first inflorescence*.—Just above ground.
*Number of flowers on young plant* (*first* 2-3 *inflorescences*).—One.
*Number of flowers on mature plant*.—Usually 3; with additional branching up to 7.
*Length of main axis*.—About 10 cm.
*Anthocyanin coloration of axis*.—Absent.
*Flower bud*.—Shape: cylindrical. Length: about 30 mm. Diameter: about 15 mm. Color: Yellow-green, RHS 144 B.
*Flower*.—Shape and Appearance: Actinomorphic, single. Number of Petals: 5. Petal length: 50-70 mm. Petal width: about 16 mm. Petal shape: spatulate. Petal surface texture: fleshy, smooth. Petal color, upper side: yellow RHS 2 C. Petal color, lower side: yellow RHS 2 D. Number of Sepals: 5. Sepal length: 6-9 mm. Sepal width: about 2 mm. Sepal thickness: about 3 mm. Sepal shape: triangular. Sepal texture: fleshy. Sepal color: Yellow-green RHS 144 B.

Peduncle:
*Length*.—10-20 mm.
*Thickness*.—14-23 mm.
*Color*.—Yellow-green, between RHS 144 A and RHS 144 B.
*Shape in cross section*.—Irregular.
*Surface*.—Ribbed.
*Pubescence*.—Absent.
*Resin*.—Milky.

Fruit:
*Fruiting season*.—Year-round.
*Weight*.—500-800 g.
*Length*.—12-13 cm.
*Diameter*.—9-10 cm.
*Shape*.—Young fruit (first 2-3 inflorescences): globose. Mature fruit: broad elliptic.
*Shape in longitudinal section*.—Elliptic.
*Shape in cross-section*.—Rounded.
*Shape of stalk end*.—Truncate.
*Depth of depression at stalk end*.—2-5 mm.
*Thickness of flesh at stalk end*.—30-40 mm.
*Diameter of ring at stalk end*.—20-25 mm.
*Height of ring at stalk end*.—1-2 mm.
*Shape of distal end*.—Rounded.
*Thickness of flesh at distal end*.—18-22 mm.
*Surface texture*.—Smooth.
*Thickness of skin*.—About 1 mm.
*Color of skin*.—Yellow-green RHS 146 B; with 10% of surface area yellow-orange RHS 23 A.
*Ridges*.—5 or 6 up to ⅓ of the fruit from the base, 3-6 cm in length and 4-5 mm high.
*Color of flesh*.—Young fruit (first 2-3 inflorescences): green RHS 137 B. Mature fruit: orange RHS 24 A.
*Thickness of flesh at middle of fruit*.—21-25 mm.
*Firmness of flesh*.—Medium firm.
*Sweetness of flesh*.—T.S.S. 13-16.5° Bx.
*Juiciness*.—Juicy.
*Taste*.—Rich; without aftertaste.
*Abundance of placenta tissue*.—Little.
*Length of cavity*.—60-75 mm.
*Width of central cavity*.—40-45 mm.
*Shape of central cavity*.—Elliptic.
*Parthenocarpy*.—Present.

Reproductive organs:
*Style*.—Absent.
*Stigma*.—Shape: propellor-shaped. Persistence of stigma: present. Diameter: 15-17 mm. Number of lobes: five. Color: yellow RHS 3 B. Length of longest lobe: 6-8 mm. Width of longest side lobe: irregular. Shape of lobe: secondary lobed.
*Ovary*.—Shape: ovoid. Length: about 30 mm. Diameter: about 20 mm. Surface: smooth. Color: light yellowish green RHS 145 B. Pubescence: absent.

Seeds: Abundant; seeds present in young plant (first 2-3 inflorescences).

Pest/disease resistance or susceptibility.—As common in *papaya* varieties.

What is claimed is:

1. A new and distinct variety of *Carica papaya* plant named 'AURORA', as illustrated and described herein.

* * * * *